United States Patent
Chen et al.

(10) Patent No.: US 9,481,905 B2
(45) Date of Patent: Nov. 1, 2016

(54) METHOD OF USING NEUTRILIZED DNA (N-DNA) AS SURFACE PROBE FOR HIGH THROUGHPUT DETECTION PLATFORM

(71) Applicant: National Central University, Jhongli, Taoyuan County (TW)

(72) Inventors: Wen-Yih Chen, Jhongli (TW); Yuh-Shyong Yang, Hsinchu (TW); Hardy Wai-Hong Chan, New Taipei (TW)

(73) Assignee: Orizhan Bioscience Limited, Taipei (TW)

( * ) Notice: Subject to any disclaimer, the term of this patent is extended or adjusted under 35 U.S.C. 154(b) by 0 days.

(21) Appl. No.: 13/770,987

(22) Filed: Feb. 19, 2013

(65) Prior Publication Data

US 2014/0235465 A1 Aug. 21, 2014

(51) Int. Cl.
*C12Q 1/68* (2006.01)
(52) U.S. Cl.
CPC .................................. *C12Q 1/6832* (2013.01)
(58) Field of Classification Search
None
See application file for complete search history.

(56) References Cited

U.S. PATENT DOCUMENTS

| | | | | |
|---|---|---|---|---|
| 4,469,863 A * | 9/1984 | Ts'o et al. | ..................... | 536/24.5 |
| 5,932,413 A * | 8/1999 | Celebuski | ..................... | 435/6.11 |
| 6,015,886 A * | 1/2000 | Dale et al. | ..................... | 536/23.1 |
| 7,264,925 B2 * | 9/2007 | Weller et al. | ................. | 435/6.16 |
| 7,534,872 B2 * | 5/2009 | Alvarado | ..................... | 536/23.1 |
| 7,667,033 B2 * | 2/2010 | Alvarado | ..................... | 536/25.3 |
| 2010/0285601 A1 * | 11/2010 | Kong | ............... | G01N 33/54306 436/94 |

FOREIGN PATENT DOCUMENTS

WO    WO 8807542 A1 * 10/1988

OTHER PUBLICATIONS

Das et al.; An Ultra Sensitive Universal Detector Based on Neutralizer Displacement, Nature Science, 2012, 4, 642-648.*
van Genderen et al. (Unusually high duplex stability for hybrids between phosphatemethylated and natural DNA with G—C base pairs, Proceedings B 91 (2), Jun. 20, 1988).*
Uslu et al. (Labelfree fully electronic nucleic acid detection system based on a field-effect transistor device, Biosensors and Bioelectronics 19 (2004) 1723-1731).*
Thiel et al. (In Situ Surface Plasmon Resonance Imaging Detection of DNA Hybridization to Oligonucleotide Arrays on Gold Surfaces, Anal. Chem. 1997, 69, 4948-4956).*
Nelson et al. (Surface Plasmon Resonance Imaging Measurements of DNA and RNA Hybridization Adsorption onto DNA Microarrays, Anal. Chem. 2001, 73, 1-7).*
Chen et al. (Improved DNA detection by utilizing electrically neutral DNA probe in field-effect transistor measurements as evidenced by surface plasmon resonance imaging, Biosensors and Bioelectronics, 41, 795-801, epub Oct. 9, 2012).*
Chen et al. (Silicon nanowire field-effect transistor-based biosensors for biomedical diagnosis and cellular recording investigation, Nano Today (2011) 6, 131-154, Mar. 8, 2011).*
Gao et al. (Silicon-Nanowire-Based CMOS-Compatible Field Effect Transistor Nanosensors for Ultrasensitive Electrical Detection of Nucleic Acids, Nano Lett. 2011, 11, 3974-3978, Aug. 17, 2011).*
Koh (Peptide Nucleic Acid (PNA) and Its Applications, Panagene Inc, Nov. 26, 2008).*
Choi (Highly Sensitive PNA Array Platform Technology for Single Nucleotide Mismatch Discrimination, J Microbiol Biotechnol. Feb. 2010;20(2):287-93).*
Nielsen (An Introduction to Peptide Nucleic Acid, Curr Issues Mol Biol. 1999;1(1-2):89-104).*
English translation of International Search Report for corresponding Taiwan Patent Application No. 101141103, completed Mar. 6, 2014 and original version in Chinese.
Wen-Yih Chen et al, "Improved DNA detection by utilizing electrically neutral DNA probe in field effect-transistor measurements as evidenced by surface plasmon resonance imaging" Biosensors and Bioelectronics vol. 41, 795-801 (2013) 795-801.
English machine translation of Taiwan Office Action Dated Mar. 7, 2014 for corresponding Taiwan Patent Application No. 101141103 and original version in Chinese.
English machine translation of Taiwan Office, Decision of Rejection Action, Dated Sep. 18, 2014 for corresponding Taiwan Patent Application No. 101141103 and original version in Chinese.

* cited by examiner

*Primary Examiner* — Aaron Priest
(74) *Attorney, Agent, or Firm* — Myers Wolin, LLC

(57) ABSTRACT

A method of using Neutrilized DNA (N-DNA) as a surface probe for a high throughput detection platform is disclosed. FET and SPRi are used as high throughput detection platforms to demonstrate that the N-DNA surface probe produces good results and enhances detection sensitivity. The N-DNA modifies the charged oxygen ions ($O^-$) on the phosphate backbone through methylation, ethylation, propylation, or alkylation, so that the backbone is not charged after this modification to increase the hybridization efficiency, sensitivity and to make the signal more clear.

10 Claims, 14 Drawing Sheets

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Synthesized E-DNA probe

<400> SEQUENCE: 1
cctcgccttc tccttgcagc tcc                                              23

<210> SEQ ID NO 2
<211> LENGTH: 23
<212> TYPE: DNA
<213> ORGANISM: Artificial Sequence
<220> FEATURE:
<223> OTHER INFORMATION: Synthesized DNA probe

<400> SEQUENCE: 2
cctcgccttc tccttgcagc tcc                                              23

<210> SEQ ID NO 3
<211> LENGTH: 23
<212> TYPE: DNA
<213> ORGANISM: Artificial Sequence
<220> FEATURE:
<223> OTHER INFORMATION: Synthesized Complementary DNA

<400> SEQUENCE: 3

```
ggagctgcaa ggagaaggcg agg                                      23

<210> SEQ ID NO 4
<211> LENGTH: 24
<212> TYPE: DNA
<213> ORGANISM: Artificial Sequence
<220> FEATURE:
<223> OTHER INFORMATION: Synthesized Noncomplementary DNA

<400> SEQUENCE: 4
agcggataac aatttcacac agga                                     24
```

METHOD OF USING NEUTRILIZED DNA (N-DNA) AS SURFACE PROBE FOR HIGH THROUGHPUT DETECTION PLATFORM

FIELD OF THE INVENTION

The present invention relates to a field of gene detection, and more specifically to a technique using Neutralized DNA (N-DNA) as a surface probe for a high throughput detection platform, and using FET and SPRi as high throughput detection platform to demonstrate that the Neutralized DNA (N-DNA) surface probe produces good results and enhances detection sensitivity.

BACKGROUND OF THE INVENTION

Gene chips are very useful in the study of gene function and recently there are many people devoting to improve the quality of the gene chips, such as sensitivity, sequence recognition capability, detection speed and operation range, etc., and one of the key achievements is the sensing probe.

Silicon Nanowire-Field Effect Transistor (SiNW-FET) has been proven as a sensor for chemical molecules or biological systems, which has the characteristics of high specificity, label-free detection, low requirement of sample amount, and fast screening. Also, its sensitivity is better than the optical detection platform. Thus, the Silicon Nanowire-Field Effect Transistor (SiNW-FET) biosensor is a platform with development potential. Nanowire FET biosensors are electrical detection platforms, which depends on external electrical fields to affect the electrical conductivity of the nanowires to determine the reaction/behavior of the biological molecules on the nanowire surface through the change of the electrical conductivity. In addition, most carriers are almost always charged, such as proteins and DNA, so when the surface carrier is disposed on the surface of the nanowire, the carrier would directly affect the conductivity of the nanowire and decrease the detection capability of the nanowire for subsequent samples. Also, nanowire FET biosensors are very sensitive to the salt concentration of the detection surface (so called debye length), and when the salt concentration of the detection surface is high, the detection length on the FET surface becomes short and the field effect becomes limited and insensitive to the surface detection.

SUMMARY OF THE INVENTION

The present invention provides a Neutralized DNA (N-DNA) surface probe for a high throughput detection platform, wherein the Neutralized DNA (N-DNA) modifies the charged oxygen ions ($O^{31}$) on the phosphate backbone of DNA via methylation, ethylation, propylation, or alkylation, so that the backbone is not charged. This modification increases the hybridization efficiency between complementary single stranded DNAs and minimizes the salt required for hybridization and then results in higher sensitivity on the detection.

E-DNA is formed through the modification of the charged oxygen ions ($O^-$) on the phosphate backbone of DNA via ethylation. E-DNA is one kind of Neutralized DNA (N-DNA) and is used to demonstrate the practice of this invention.

A method to verify the effect of Neutralized DNA (N-DNA) surface probe for a high throughput detection platform may include steps of a chip modification step and a fluid detection step. Also, the present invention uses the FET platform and the SPRi platform as embodiments for high throughput detection platforms to demonstrate that Neutralized DNA (N-DNA) surface probe has better detection results.

DETAILED DESCRIPTION OF THE INVENTION

Figure 1A:
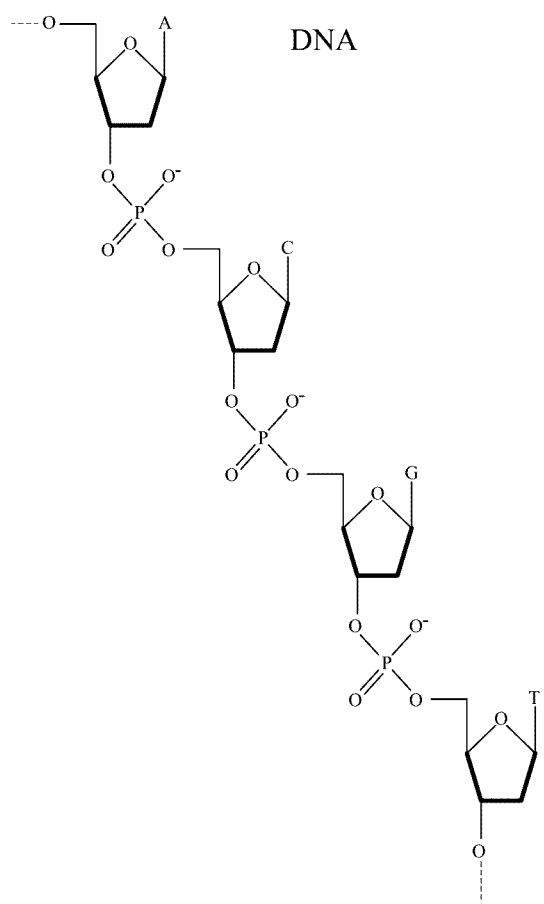
FIGS. 1A to 1C illustrate a schematic view of DNA, N-DNA and E-DNA.
Figure 1B:
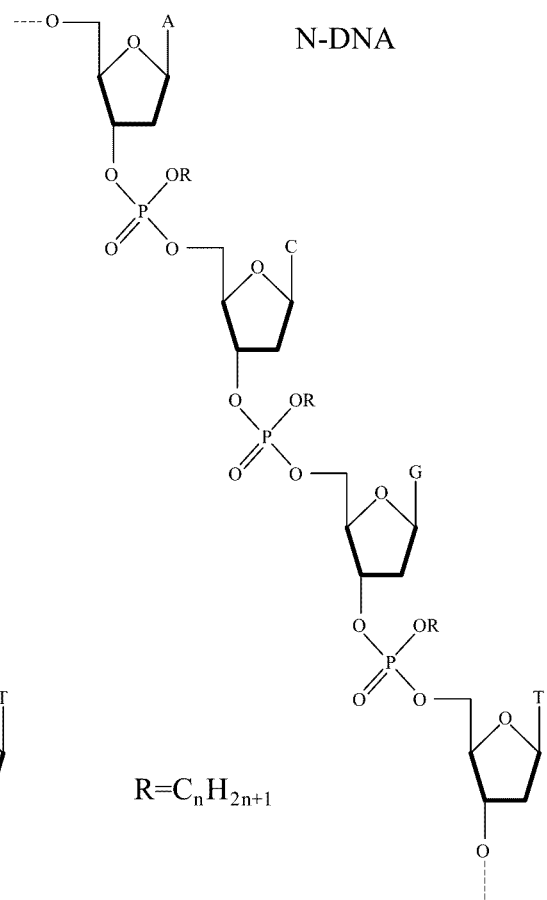
Figure 1C:
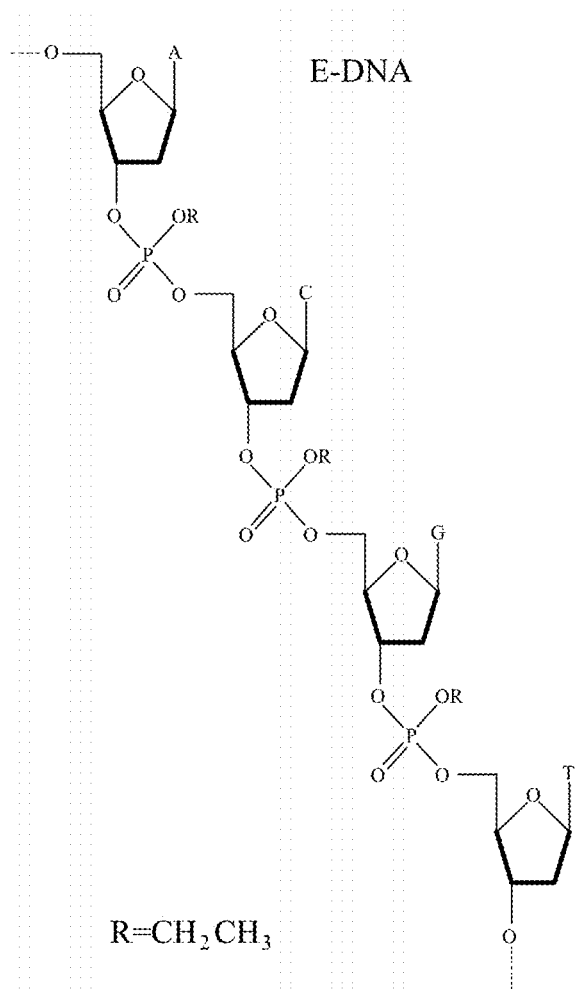

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications that might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

The present invention provides a Neutralized DNA (N-DNA) surface probe for a high throughput detection platform, wherein the Neutralized DNA (N-DNA) modifies the charged oxygen ions (O$^-$) on the phosphate backbone of DNA via methylation, ethylation, propylation, or alkylation, so that the backbone is not charged after this modification to increase the hybridization efficiency, sensitivity and to make the signal more clear. Also, the Neutralized DNA (N-DNA) includes E-DNA, which is formed through the modification of the charged oxygen ions (O$^-$) on the phosphate backbone of DNA via ethylation. The present invention uses E-DNA as embodiments for experiments and verifications, but does not use it to limit the present invention. Also, the present invention hopes to compare the interaction between different kinds of charged DNA probes and complementary DNA. In order to minimize the effect of single-strand DNA secondary structure, the probe design in the present invention focuses on the DNA sequences without intramolecular secondary structure. Also, considering the application of the probes, the present invention designs E-DNA sequences as shown in Table 1, which is only used for experiments, not used to limit the present invention. To further understand whether E-DNA has the hybridization capability as general DNAs, the present invention uses Circular Dichroism to detect the samples of E-DNA, DNA, Complementary DNA, E-DNA/Complementary DNA mixture and DNA/Complementary DNA mixture with the same DNA concentration (1 µM), heats up these two strands of DNAs to 95° C., cools them down to the room temperature and compares the peak difference between these samples. The nuclear acid sequences and characteristics are shown in Table 1:

TABLE 1

| Sequence Name | Sequence | MW (g/mole) | Tm (° C.) |
|---|---|---|---|
| E-DNA probe | 5'NH 2-CCTCGCCTTCTCCTTGCAGCTCC-3' | 7,655.60 | 75.0 |
| DNA probe | 5'NH 2-C + C + T + C + G + C + C + T + T + C + T + C + C + T + T + G + C + A + G + C + T + C + C-3' | 7,017.60 | 75.0 |
| Complementary DNA | GGAGCTGCAAGGAGAAGGCGAGG | 7,252.77 | 75.0 |
| Noncomplementary DNA | AGCGGATAACAATTTCACACAGGA | 7,378.9 | 54.0 |

Figure 2A:
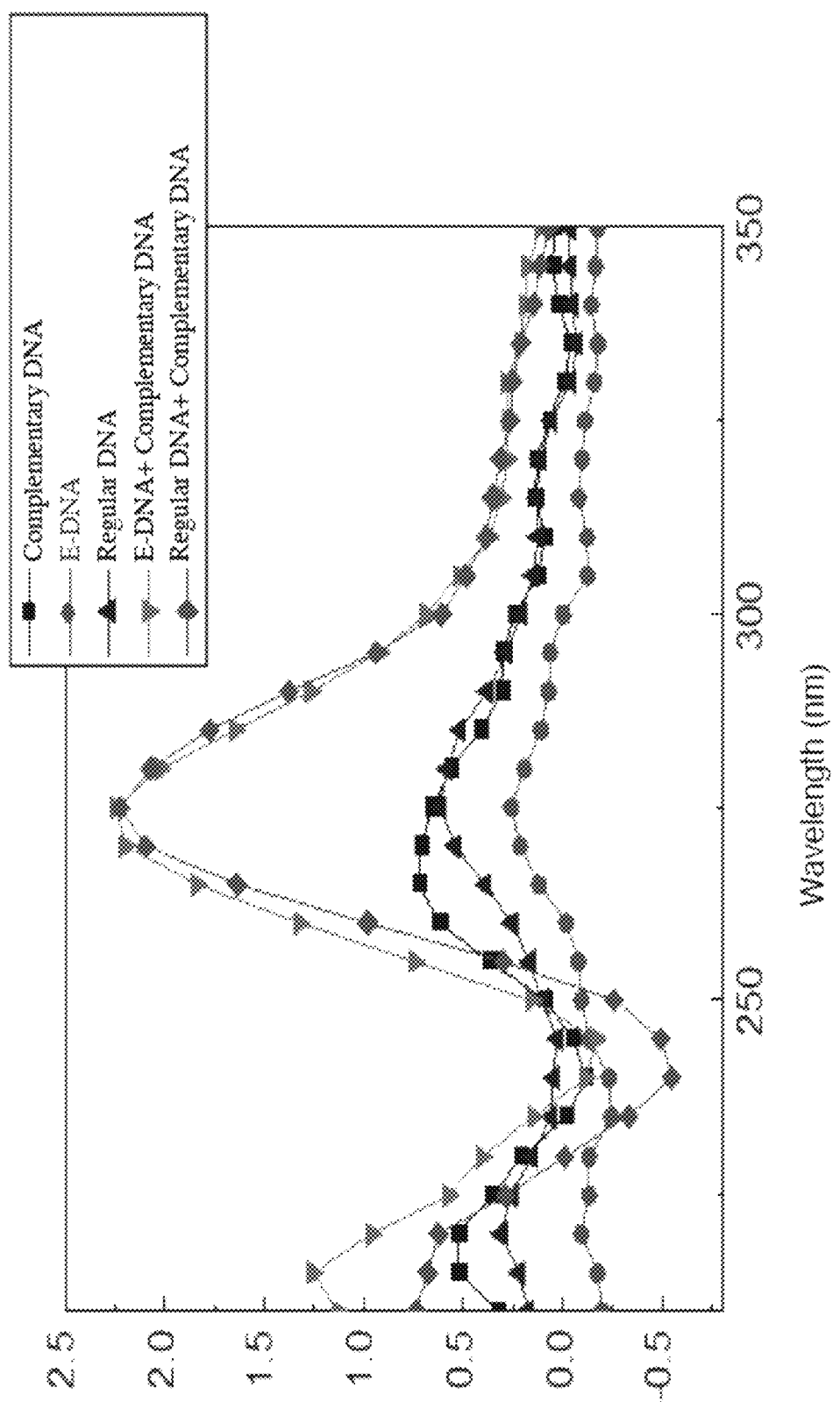
FIG. 2A illustrates characteristic peaks of E-DNA, DNA, Complementary DNA, E-DNA/Complementary DNA mixture, and DNA/Complementary DNA mixture using Circular Dichroism.
Figure 2B:
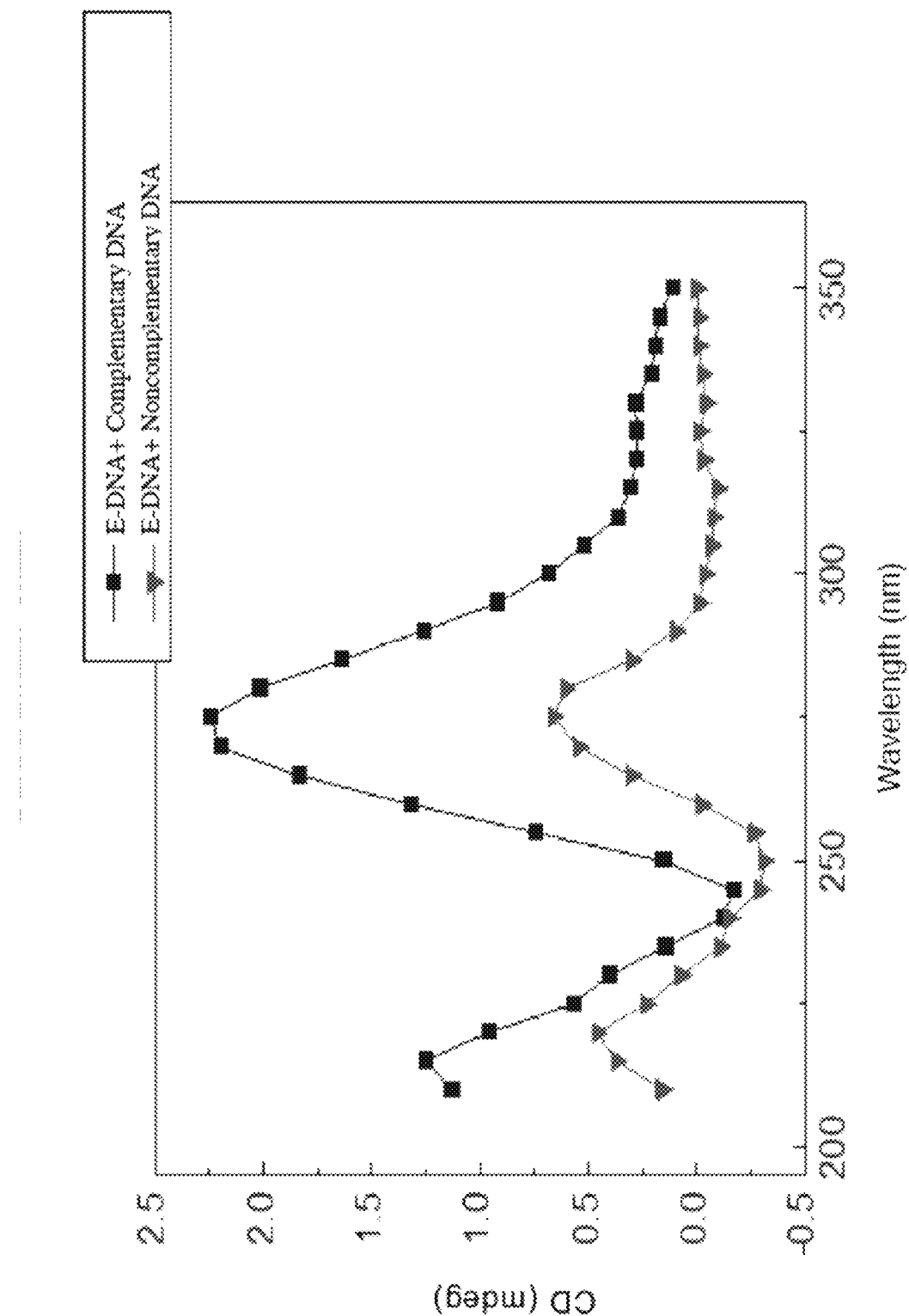
FIG. 2B illustrates characteristic peaks of E-DNA/Complementary DNA mixtures and non-complementary DNA mixtures using CD.

The measurement results are shown in FIG. 2A, and the characteristic peak position of each sample at about the wavelength of 245 nm has a negative peak, and a positive peak near the wavelength of 280 nm, which represents the DNA secondary structure (B-form double helix) in these samples. Further comparing the characteristic peaks, it shows that the strength of characteristic peaks of E-DNA/Complementary DNA mixture and DNA/Complementary DNA mixture is greater than another three single-stranded DNA samples, meaning that the E-DNA/Complementary DNA mixture and DNA/Complementary DNA mixture have more DNA B-form structure than another three single strand DNA samples. The double-stranded DNA has three forms: B-form, A-form and Z-form, which are different from each other in their bonding angle and the degree of hydration. Experimental results show that even single-stranded DNA has a characteristic peak near the wavelength of 245 nm and 280 nm. It is mainly because single-stranded DNAs try to reduce its own energy in the solution, and they are inclined to use partially complementary fragments of sequence base pairs to form hairpin structures through hybridization. When DNA hybridizes, the secondary structure of single-stranded DNA would be first destroyed and then forms a double helix structure. The present invention uses characteristic peak to explain that although single-stranded DNA has B-form, the existence of B-form is only in the stem of the hairpin structure, which is weaker than double-stranded B-form DNA after hybridization. Therefore, the results can be used to determine whether two DNA samples conduct hybridization by comparing the strength of the characteristic peaks with two single-stranded DNA samples. From the experimental results in FIG. 2A, it is observed that the strength of the characteristic peak of two DNA mixtures are stronger than three samples of single-stranded DNA, which means that E-DNA and Complementary DNA do conduct hybridization. The present invention is trying to further confirm whether the hybridization has specificity in sequence recognition. As shown in FIG. 2B, the characteristic peak of E-DNA/Complementary DNA is greater than that of two non-complementary DNA samples, meaning that after hybridization, E-DNA and complementary DNA would form a double helix structure while E-DNA and non-complementary DNA have no hybridization. This demonstrates that E-DNA hybridization does have the capability of sequence recognition. The present invention uses Circular Dichroism to demonstrate that (1) E-DNA does have the capability of hybridization, and (2) the hybridization is specific, and thus E-DNA is capable of being molecular probes of biological sensors.

After verifying E-DNA's hybridization capability as the potential to be probes, the present invention further provides a method of using E-DNA as a surface probe for a high throughput detection platform, the method including a chip modification step and a fluid detection step. The present invention uses uncharged DNAs such as E-DNA as surface probes, and then utilizes Field-effect transistor (FET) detection platform and Surface Plasmon Resonance Imaging (SPRi) detection platform as high throughput detection platforms to verify the effect of E-DNA thereon, and the present invention is not limited by these two platforms.

Applying E-DNA on a FET detection platform may include:

1. Chip modification step: step 1: an unmodified FET chip is disposed on a carrier of the FET device to check whether the conductivity of the FET chip is normal for subsequent modification; step 2: soaking the FET chip in each acetone and alcohol for 15 minutes, washing and drying the chip with nitrogen; step 3: soaking the FET chip in 2% (v/v) APTES solution for 20 minutes, washing it with alcohol and drying the chip with nitrogen; step 4: placing the FET chip on a heating device to heat to 120° C. for 10 minutes, washing it with deionized water and drying with nitrogen; step 5: soaking the FET chip in valeraldehyde solution 2.5% (v/v) for one hour, washing it with deionized water and drying with nitrogen; step 6: placing the FET chip in the probe solution of modified amino group for 16 hours, washing it after the reaction with deionized water and drying with nitrogen; and step 7: soaking the FET chip in 50 mM ethanolamine solution for 2 hours, washing it with deionized water and drying with nitrogen.

2. Fluid detection step: step 1: after immobilizing E-DNA probes on the FET chip, placing the FET chip on the carrier to determine whether the conductivity of the chip still meets the experimental standard; step 2: attaching PDMS microfluidic channels on the FET chip, introducing buffer solution into the channels and measuring conductivity of the FET chip; step 3: replacing the buffer solution in the channels with non-complementary DNA solution, and measuring conductivity of the FET chip after placing the chip for 5 minutes; and step 4: using buffer solution to clean the FET chip and channels, introducing complementary DNA solution into the channels, and measuring conductivity of the FET chip after placing the chip for 5 minutes.

Figure 3A:
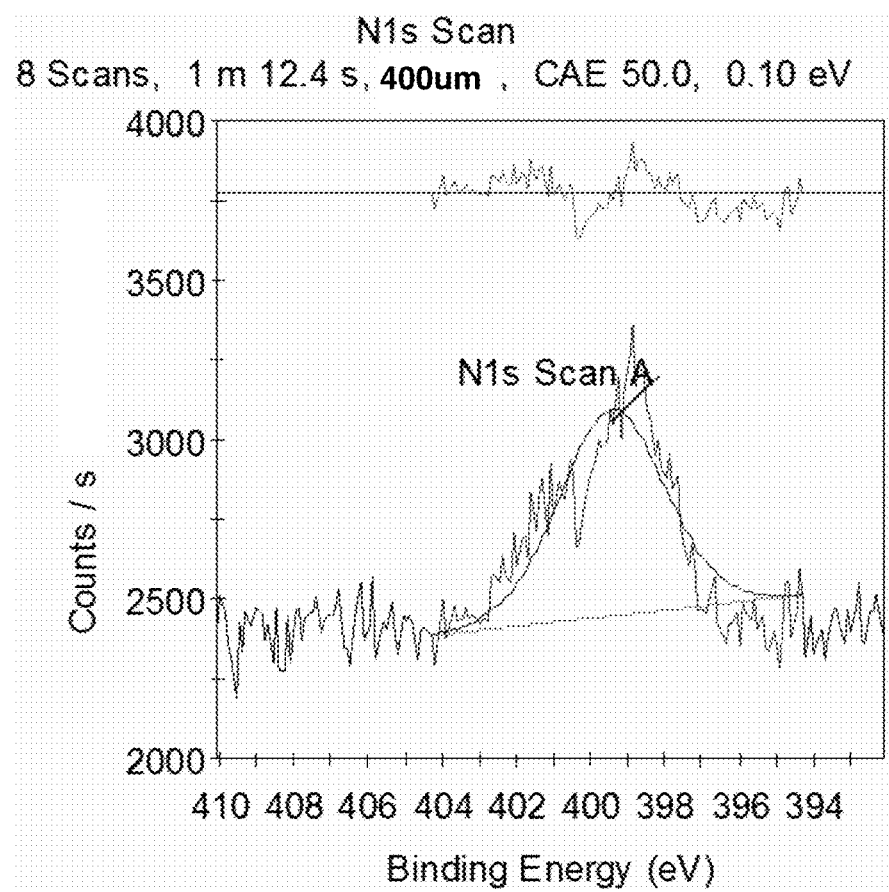
FIG. 3A illustrates ESCA analysis of nitrogen element content on the surface of the FET chip with immobilized E-DNA probes.
Figure 3B:
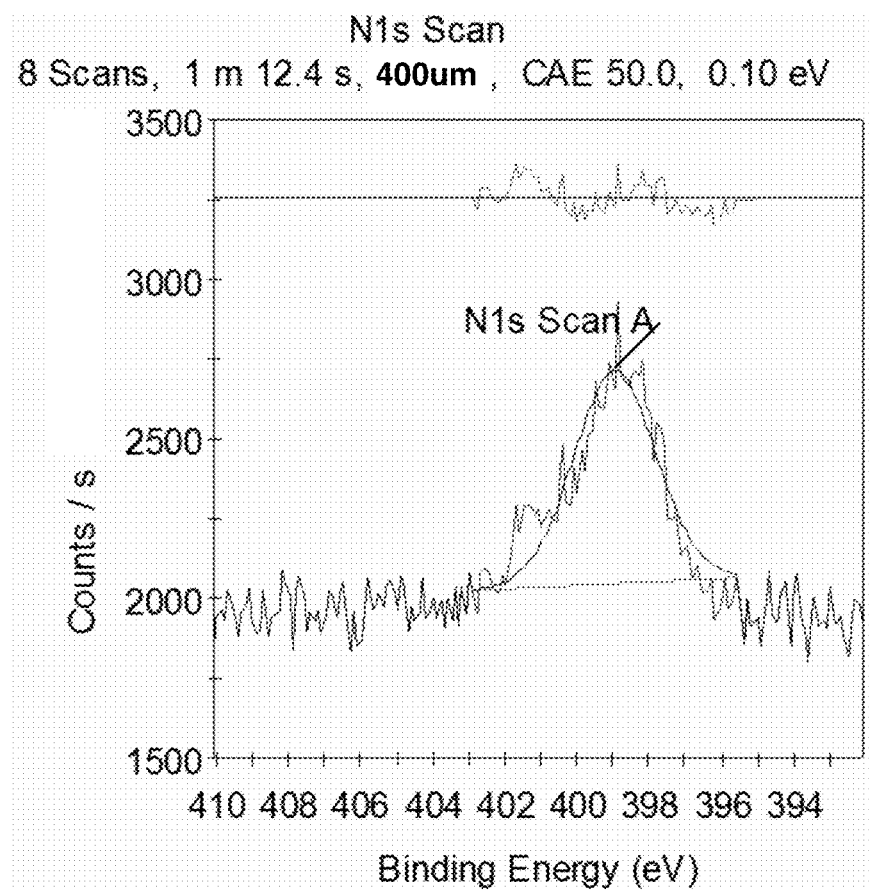
FIG. 3B illustrates ESCA analysis of nitrogen element content on the surface of the FET chip with immobilized DNA probes.

In order to determine whether the probes are successfully immobilized on the chip surface, the present invention utilizes electron spectroscopy for chemical analysis (ESCA) as a detection platform to check whether the surface modification is successful. The material of the FET chip is silicon, and when the DNA probe or E-DNA probe is immobilized on the chip surface, the surface of the FET chip would have an extra nitrogen element due to the nitrogen element at the DNA base portion. Therefore, the existence of the nitrogen element can be used to determine whether DNA is on the chip surface. FIG. 3A shows ESCA analytical results after immobilizing E-DNA probes on the chip surface, and FIG. 3B shows ESCA analytical results after immobilizing DNA probes on the chip surface.

Figure 4A:
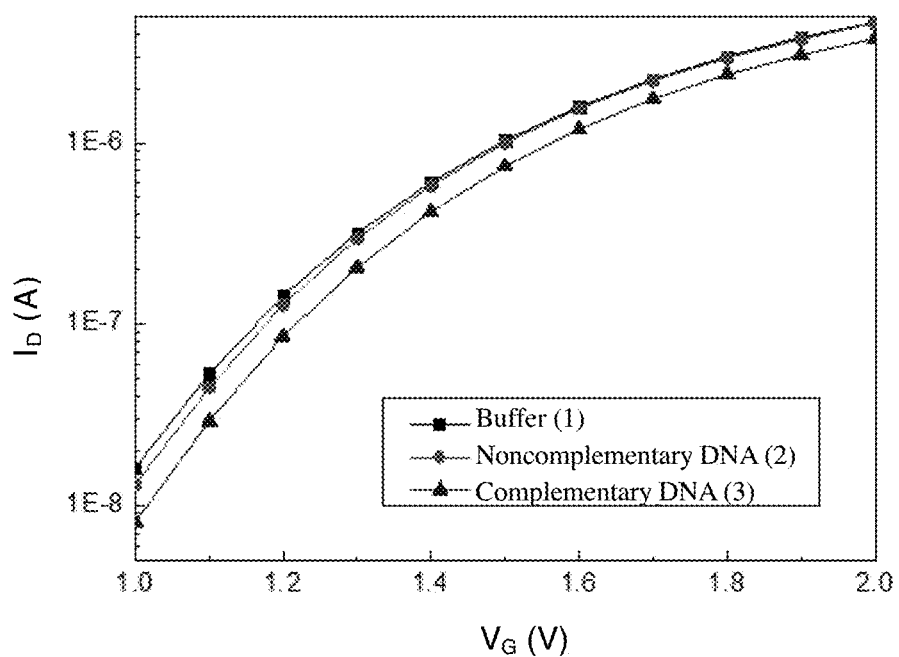
FIG. 4A illustrates current signal change for different samples using FET.
Figure 4B:
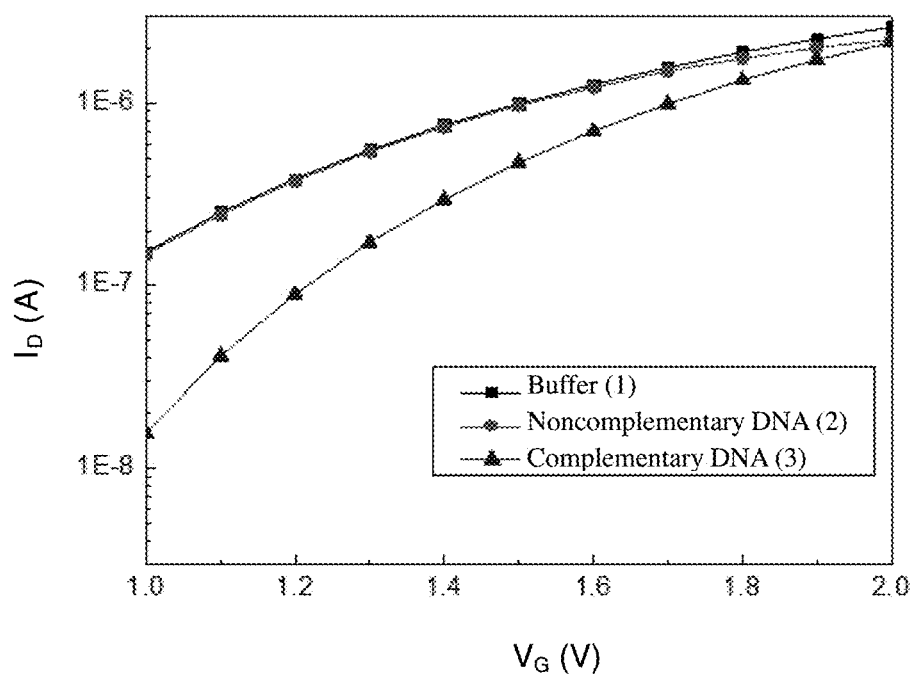
FIG. 4B illustrates current signal change for different samples using FET.

The present invention uses n-type Silicon Nanowire-Field Effect Transistor (SiNW-FET) biosensors as detection platforms, and immobilizes surface probes on silicon nanowire through covalent boding. Buffer solution, complementary DNA and non-complementary DNA are introduced to the surfaces of two different probes. As shown in FIGS. 4A, 4B, three curves are $V_G$-$I_D$ curves. $V_G$ is a positive bias from the gate, and $I_D$ is the current from source to drain in the element. Since the present invention uses n-type Silicon Nanowire-Field Effect Transistor (SiNW-FET), when $V_G$ is increasing gradually, it induces more electron carriers (electrons) from the nanowire to increase the conductivity thereof, and further increase the current ($I_D$) from source to drain. According to the results of analytical experiments, major electron carriers in the nanowire are electrons in the n-type Silicon Nanowire-Field Effect Transistor (SiNW-FET), so if the DNAs in the sample hybridize with the surface probes, the electric field of the complementary DNAs on the surface would induce the silicon nanowire to generate positive-charged carriers (holes). However, positive-charged carriers and major electron carriers (electrons) in the nanowires are opposite in terms of charge, the positive-charged and negative-charged carriers are cancelled with each other. Electrons are still major carriers in the nanowires, however, since the electrons are cancelled with the holes induced from target molecules, the number of major electron carriers (electrons) in the nanowires is reduced, and conductivity thereof is further reduced, so the current ($I_D$) from source to drain decreases. According to the experimental data, when the solution on the surface of the nanowires with surface probes is replaced from buffer solution to non-complementary DNA, the curve slightly goes down. When the solution is changed to complementary DNA, the curve goes down even more. This phenomenon can be observed in both uncharged DNA (E-DNA) and DNA probes, which means that the complementary DNAs do hybridize with probes to change the conductivity of the nanowires. On the other hand, the non-complementary DNAs cannot hybridize with the probes, so they are hard to attach to the surface. However, the experimental results show that even with the non-complementary DNAs, the conductivity of the nanowires may still change slightly, which results from non-specificity of the samples attaching to the surface. Furthermore, nanowire FET is an electrical detection platform, it is very sensitive to the charged molecules. Thus, if the surface carrier is charged, it would generate a greater background noise to significantly decrease the detection capability and further affect the sensitivity to subsequent samples. So, when using E-DNA as surface probes, the background noise can be effectively controlled to increase the detection sensitivity.

Applying E-DNA on a SPRi detection platform may include:

1. Chip modification step: step 1: using 95% (v/v) ethanol, deionized water and 95% (v/v) ethanol to wash the SPRi chip and drying it with nitrogen; step 2: using UV ozone cleaning machine to cleaning the SPRi chip for 20 minutes; step 3: using 95% (v/v) ethanol, deionized water and 95% (v/v) ethanol to wash the SPRi chip and drying it with nitrogen; step 4: soaking the chip in 1 mM ethanol solution with thiols molecules for 16 hours, using 10% (v/v) $NH_4OH$ and 95% (v/v) ethanol to washing the chip and drying it with nitrogen.

2. Fluid detection step: step 1: introducing buffer solution and waiting for the system to reach a steady state; step 2: introducing EDC/NHS (0.1 mM/0.025 mM) solution for 15 minutes, activating the carboxyl group on the surface of the SPRi chip, and washing with buffer solution; step 3: introducing E-DNA probes or DNA probes with modified uncharged amino group from several different channels, placing the solution (40% (v/v) glycerol) of single-stranded DNAs with modified amino group 40 μM on the surface of the SPRi chip for 4 hours to immobilize the probes on the SPRi chip and introducing buffer solution to wash probes that do not attach to the SPRi chip surface; step 4: introducing 10 mM ethanolamine for 30 minutes to cover the surface that does not have the carboxyl group of the probes, and washing with buffer solution; step 5: introducing complementary DNAs into the channels to hybridize with the surface probes, and introducing buffer solution again to wash out unreacted DNAs; step 6: comparing surface absorbing situations of different probes and further comparing the situation of different probes reacting with complementary DNAs.

Figure 5A:
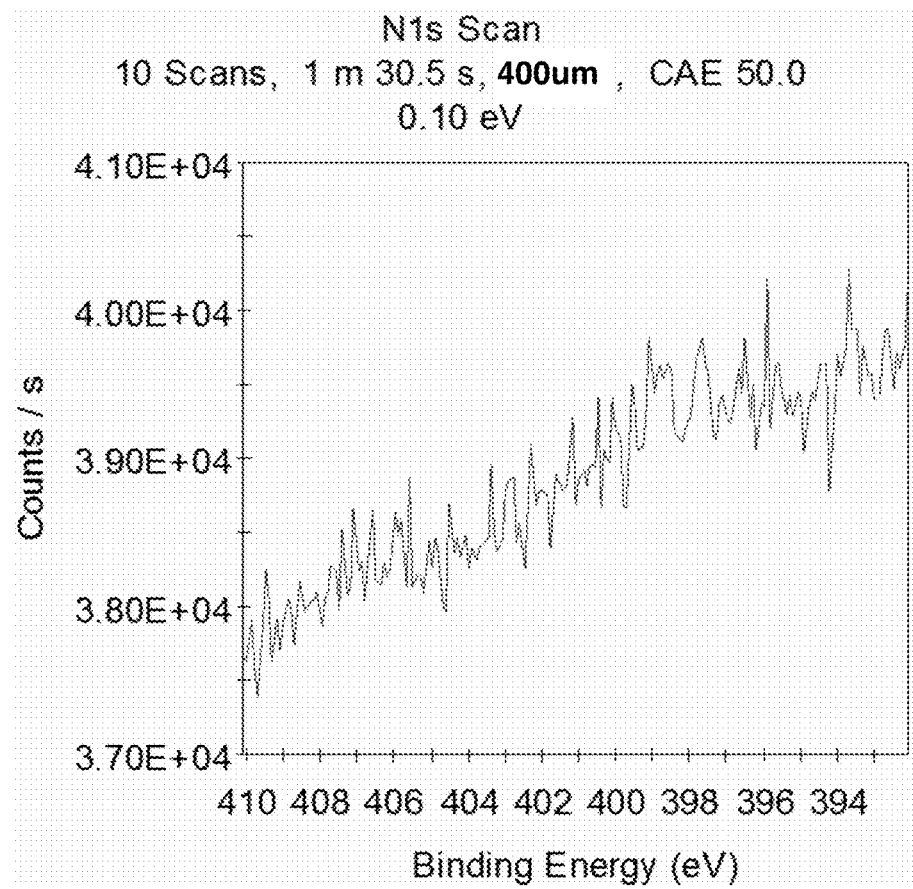
FIG. 5A illustrates ESCA analytical results in which no DNA probes immobilized on the chip surface, and the surface is only modified by thiol molecules and carboxyl functional group for surface modification.
Figure 5B:
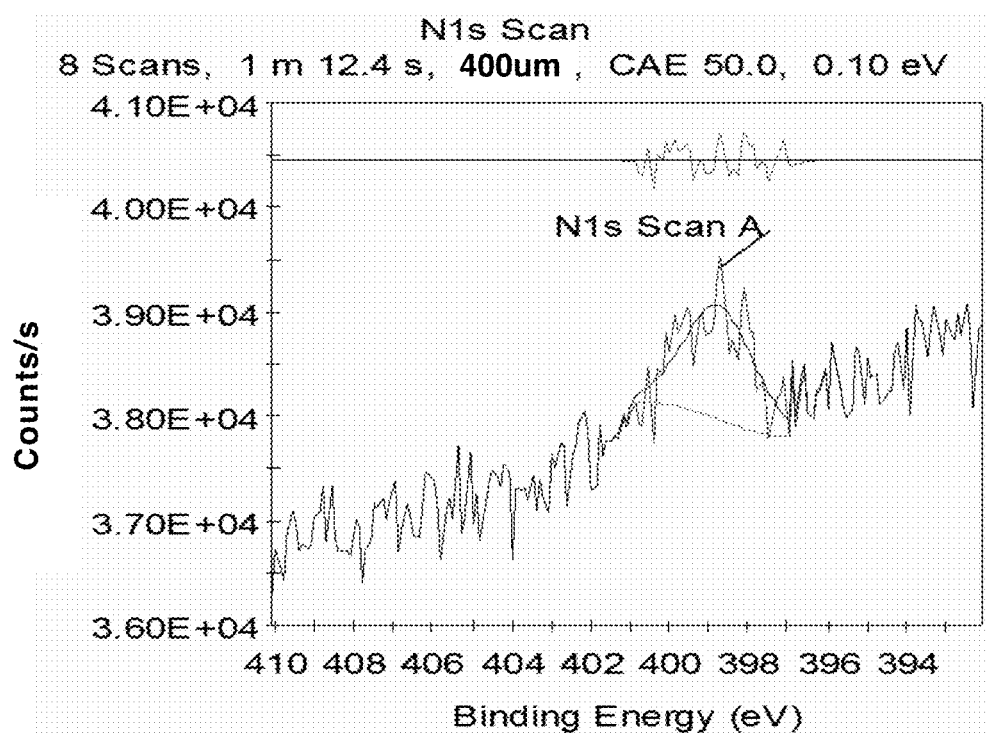
FIG. 5B illustrates ESCA analysis of nitrogen element content on the surface of the SPRi chip.
Figure 5C:
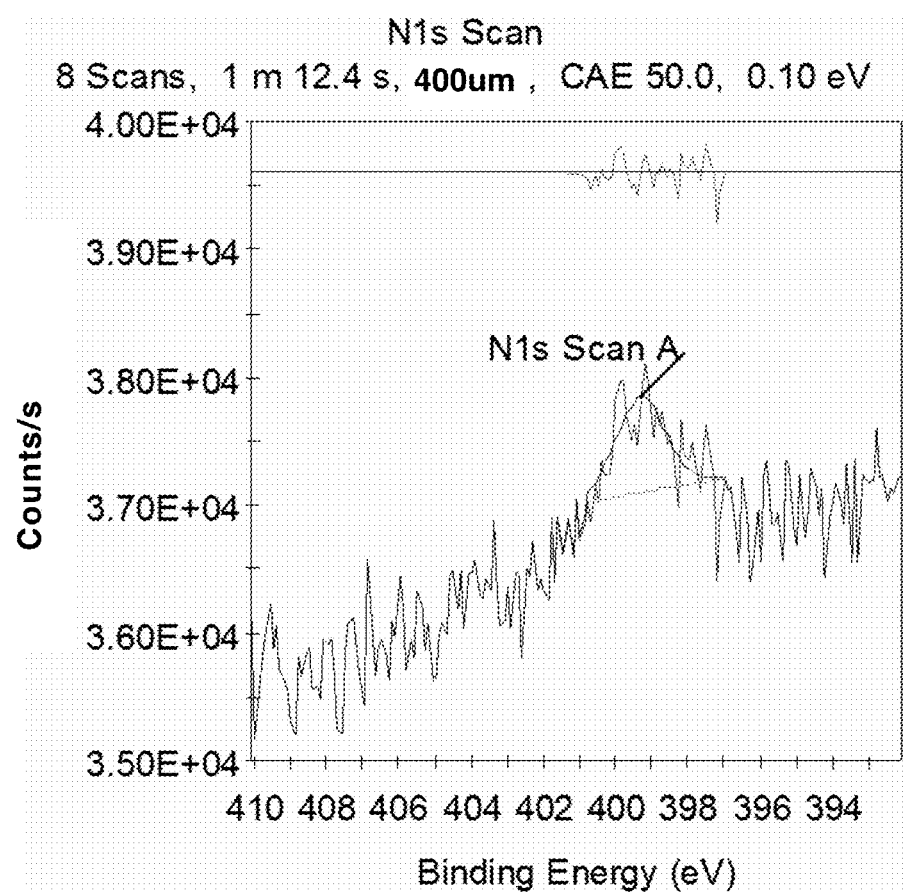
FIG. 5C illustrates ESCA analysis of nitrogen element content on the surface of the SPRi chip.

To assure that the probes are successfully immobilized on the chip surface, the present invention uses ESCA as a detection platform. Gold is used for the SPRi chip and after DNA probes or E-DNA probes are immobilized on the chip surface, more and more nitrogen elements can be found on the surface of the SPRi chip because the bases of the DNA contain nitrogen element. Therefore, the existence of nitrogen element can be used to determine whether the DNA is immobilized on the chip surface. FIG. 5A shows the results of ESCA for the chip surface modified by thiol molecules and carboxyl functional group, and FIG. 5B shows the ESCA results after immobilizing E-DNA probes. FIG. 5C shows the ESCA results after immobilizing DNA probes.

Figure 6A:
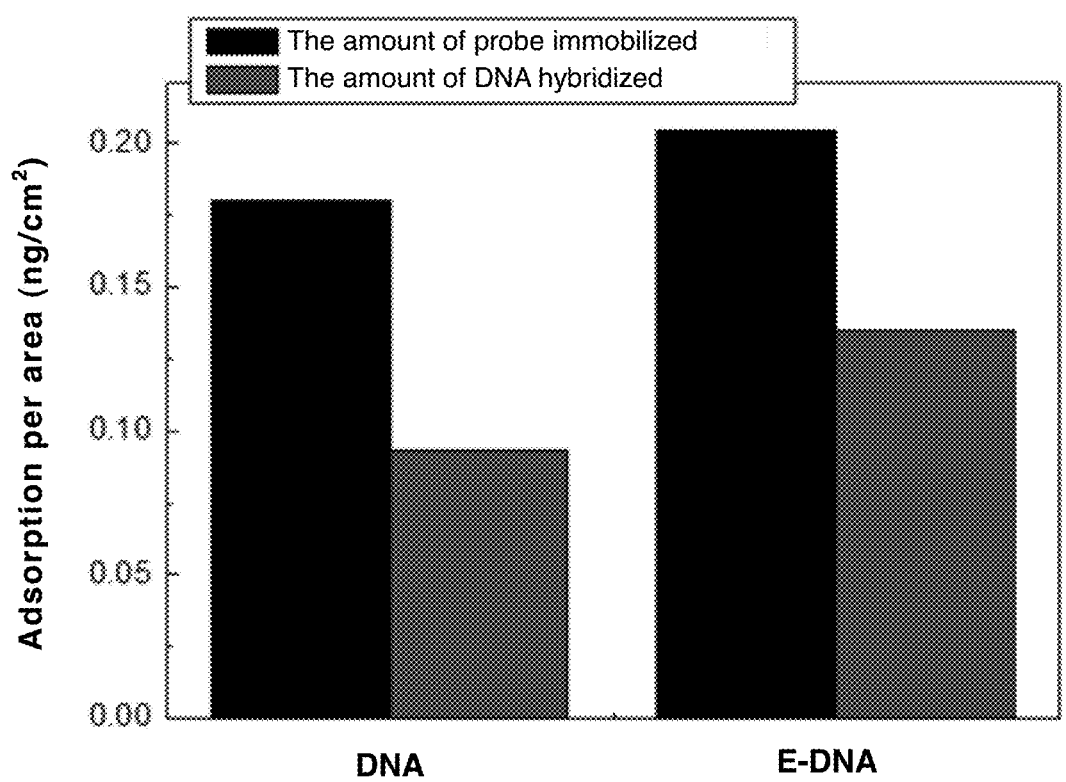
FIG. 6A illustrates the hybridization amount of the probes and targets on the chip surface through the SPRi detection platform.
Figure 6B:
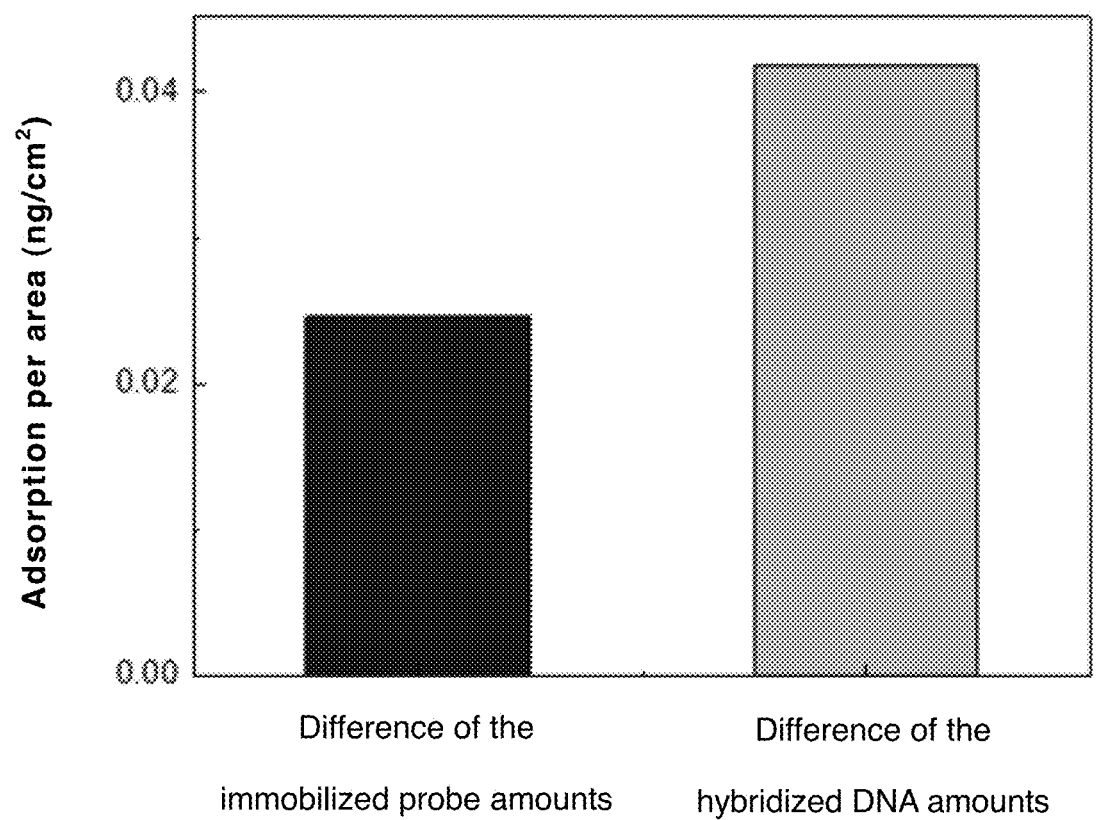
FIG. 6B illustrates the differences of the amount of probe immobilization and the differences of the hybridization amount of complementary DNA through the SPRi detection platform.
Figure 6C:
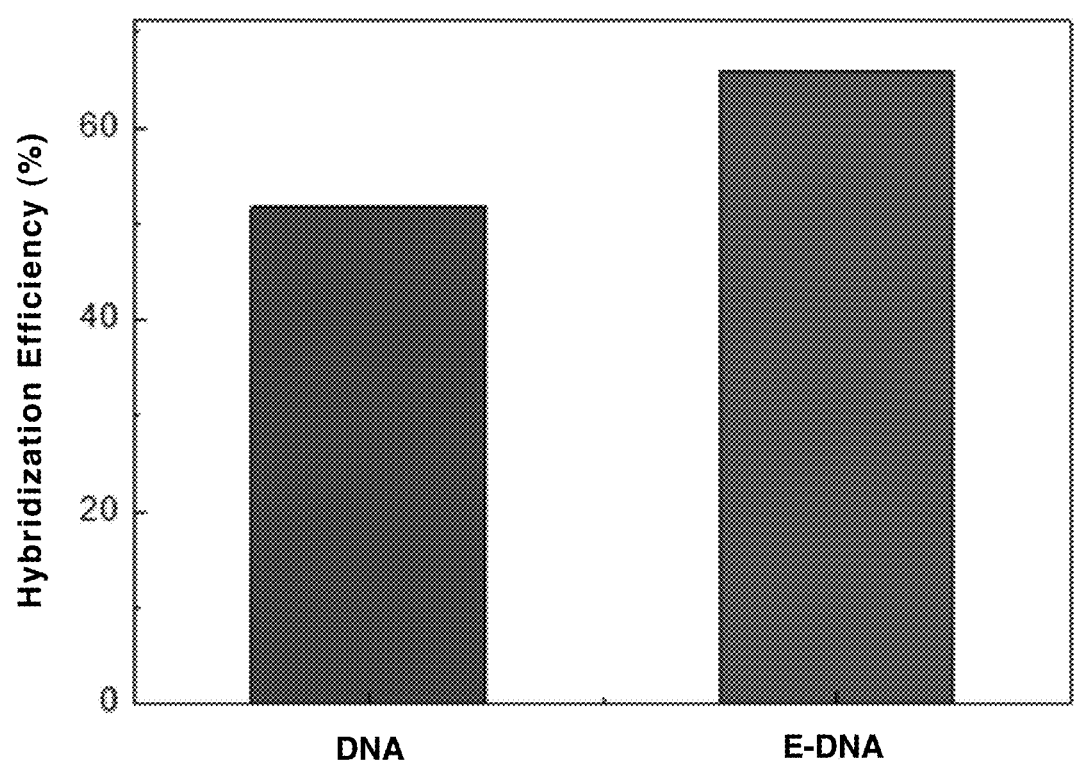
FIG. 6C illustrates the hybridization rate of E-DNA/complementary DNA and DNA/complementary DNA through the SPRi detection platform.

As can be seen in FIG. 6A, when E-DNAs are used as probes, the absorption amount of both probes and complementary DNAs is higher than that when using DNAs as probes, which means when using E-DNAs as probes, the immobilization amount on the chip surface will be more comparing with using DNA probes. Furthermore, when using E-DNA probes, the hybridization amount with complementary DNA can be more comparing with using DNA probes, meaning that the immobilization amount of the probes can affect the hybridization amount of the probes and complementary DNA. The phenomena may be the reason that when E-DNA probes are immobilized on the chip surface, since the probes are not charged, there is no electrostatic repulsion between the probes, so that when the probes are immobilized on the chip surface, the spacing between probes is small. Generally, there is electrostatic repulsion between DNA probes, so the spacing is larger between probes on the chip surface. In other words, for the same area, the amount of E-DNA probes would be more than DNA probes, as well as the immobilization amount. Furthermore, the present invention subtracts the immobilization amount of two different probes comparing with the subtracted hybridization amount of two different probes and the complementary DNAs, and the results are shown in FIG. 6B, wherein the subtracted hybridization amount of two different probes and the complementary DNAs are much greater than the immobilization amount of two different probes, meaning that the reason why the hybridization amount of E-DNA/complementary DNA is higher than that of DNA/complementary DNA is not only due to more E-DNA immobilized on the chip surface. Therefore, the present invention further compares the Hybridization Rate (Hybridization Rate=complementary DNA density/DNA probe density ×100%) of two different probes to obtain the hybridization rate of two different probes and complementary DNAs, as shown in FIG. 6C. According to the results, the hybridization rate of E-DNA probes and complementary DNAs is better than DNA probes, meaning that the hybridization amount of E-DNA probes/complementary DNAs is more than DNA probes/complementary DNAs. Under such circumstances, when E-DNA probes are used on SPRi, the detection signal is better than DNA probes because (1) E-DNA probes have more immobilization amount on the chip than DNA probes, and (2) the hybridization rate of E-DNA probes/complementary DNAs is better than DNA probes/complementary DNAs.

Accordingly, the present invention uses E-DNA as surface probes and applies to FET and SPRi detection platforms, both of which demonstrate that E-DNA has great detection results. So, using N-DNA (uncharged DNA) as surface probes on a high throughput detection platform can effectively reduce the background noise of the system, and enhance detection sensitivity.

Having described the invention by the description and illustrations above, it should be understood that these are exemplary of the invention and are not to be considered as limiting. Accordingly, the invention is not to be considered as limited by the foregoing description, but includes any equivalents.

What is claimed is:

1. A high throughput detection platform comprising a neutralized DNA (N-DNA) probe of formula (I):

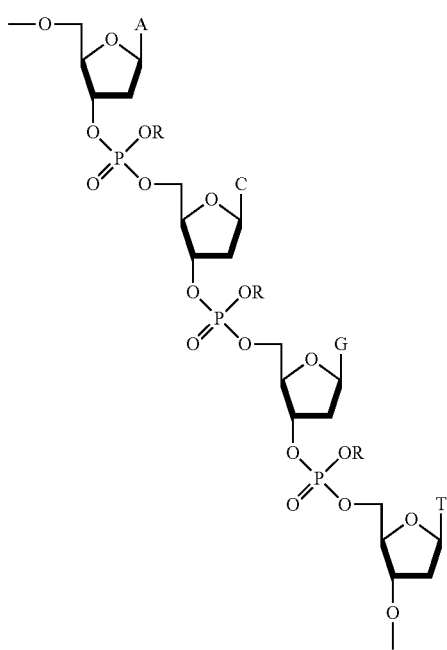

$R = C_nH_{2n+1}$ wherein n is 1, 2, or 3 and each A, T, G, and C is any of adenine, thymine, guanine, and cytosine;
wherein said probe can hybridize to a complementary target nucleic that is to be detected; and
wherein said probe is covalently attached to a solid surface, said solid surface is that of a silicon nanowire field effect transistor (SiNW-FET).

2. The detection platform of claim 1, wherein R is methyl, ethyl, or propyl.

3. The detection platform of claim 2, wherein R is ethyl.

4. The detection platform of claim 1, wherein the transistor is an n-type transistor.

5. The detection platform of claim 4, wherein hybridization of a complementary target nucleic acid to the neutral DNA probe results in a decrease in current flow from source to drain of the field effect transistor, wherein said decrease is greater than that observed when said probe is contacted with a non-complementary nucleic acid.

6. The detection platform of claim 1, wherein the transistor is an p-type transistor.

7. The detection platform of claim 6, wherein hybridization of a complementary target nucleic acid to the neutral DNA probe results in an increase in current flow from source to drain of the field effect transistor, wherein said increase is greater than that observed when said probe is contacted with a non-complementary nucleic acid.

8. A method of covalently attaching an N-DNA probe to a SiNW-FET transistor to provide the high throughput detection platform of claim 1, the method comprising:
   step 1: disposing an unmodified SiNW-FET chip on a carrier of the SiNW-FET device to check whether the conductivity of the SiNW-FET chip is normal for subsequent modification;
   step 2: soaking the SiNW-FET chip of step 1 in each of acetone and alcohol for 15 minutes, washing and drying the chip with nitrogen;
   step 3: soaking the SiNW-FET chip of step 2 in 2% (v/v) APTES solution for 20 minutes, followed by washing with alcohol and drying with nitrogen;
   step 4: placing the SiNW-FET chip of step 3 on a heating device to heat to 120° C. for 10 minutes, followed by washing with deionized water and drying with nitrogen;
   step 5: soaking the SiNW-FET chip of step 4 in valeraldehyde solution 2.5% (v/v) for one hour, followed by washing with deionized water and drying with nitrogen;
   step 6: placing the SiNW-FET chip of step 5 in a solution of said N-DNA probe comprising a modified amine group for 16 hours, followed by washing with deionized water and drying with nitrogen;
   step 7: soaking the SiNW-FET chip of step 6 in 50 mM ethanolamine solution for 2 hours, followed by washing with deionized water and drying with nitrogen to provide a SiNW-FET chip comprising immobilized N-DNA probes; and
   step 8: subjecting the SiNW-FET chip of step 7 to a fluid detection step.

9. The method of utilizing N-DNA surface probe in a high throughput detection platform of claim 8, wherein the high throughput detection platform is an FET detection platform, and the chip modification step includes steps of step 1: an unmodified FET chip is disposed on a carrier of the FET device to check whether the conductivity of the FET chip is normal for subsequent modification; step 2: soaking the FET chip in each acetone and alcohol for 15 minutes, washing and drying the chip with nitrogen; step 3: soaking the FET chip in 2% (v/v) APTES solution for 20 minutes, washing it with alcohol and drying the chip with nitrogen; step 4: placing the FET chip on a heating device to heat to 120° C.

for 10 minutes, washing it with deionized water and drying with nitrogen; step 5: soaking the FET chip in valeraldehyde solution 2.5% (v/v) for one hour, washing it with deionized water and drying with nitrogen; step 6: placing the FET chip in the probe solution of modified amine for 16 hours, washing it after the reaction with deionized water and drying with nitrogen; and step 7: soaking the FET chip in 50 mM ethanolamine solution for 2 hours, washing it with deionized water and drying with nitrogen.

10. The method of claim 8, wherein the fluid detection step comprises:
   step 1: placing the SiNW-FET chip comprising immobilized N-DNA probes on the carrier to determine whether the conductivity of the chip still meets the experimental standard;
   step 2: attaching PDMS microfluidic channels on the SiNW-FET chip of step 1, introducing buffer solution into the channels and measuring conductivity of the SiNW-FET chip;
   step 3: replacing the buffer solution in the channels on the SiNW-FET chip of step 2 with non-complementary DNA solution, and measuring conductivity of the SiNW-FET chip after placing the chip for 5 minutes; and
   step 4: cleaning the SiNW-FET chip and the channels of step 3 with buffer solution, introducing complementary DNA solution into the channels, and measuring conductivity of the SiNW-FET chip after placing the chip for 5 minutes.

* * * * *